United States Patent [19]

Ogawa

[11] 4,411,525

[45] Oct. 25, 1983

[54] METHOD OF ANALYZING AN OBJECT BY USE OF SCATTERING LIGHT

[75] Inventor: Tomoya Ogawa, Tokyo, Japan

[73] Assignee: Fuji Photo Optical Co., Ltd., Japan

[21] Appl. No.: 291,935

[22] Filed: Aug. 11, 1981

Related U.S. Application Data

[63] Continuation of Ser. No. 9,496, Feb. 5, 1979, abandoned.

[30] Foreign Application Priority Data

Feb. 8, 1978 [JP]  Japan .................................. 53-13293

[51] Int. Cl.³ ........................................... G01N 21/49
[52] U.S. Cl. ................................... 356/339; 356/318
[58] Field of Search ............... 356/301, 308, 338, 339, 356/30, 317, 318

[56] References Cited

U.S. PATENT DOCUMENTS 4,030,827 6/1977 Delhaye et al. ..................... 356/301
4,049,350 9/1977 Brück .................................... 356/30

FOREIGN PATENT DOCUMENTS 2727265 5/1978 Fed. Rep. of Germany ...... 356/301

OTHER PUBLICATIONS

Vzgiris, "Sensitive Optical Heterodyne Method for Light Scattering Studies", *Rev. Sci. Instru*, vol. 43, No. 9, pp. 1383-1385, Sep. 1972.
Shepherd, "Raman Scattering Techniques Applied to Problems in Solid State Physics", *Applied Optics*, vol. 11, No. 9, pp. 1924-1927, Sep. 1972.
Fowler et al., "Analytical Technique for Probing and Controlling Gas Composition in Chemical Processes", *IBM Tech. Discl. Bull.*, vol. 15, No. 12, pp. 3885-3886, May 1973.
Okada et al., "Signal-to-Noise Ratio Improvement . . .", *J. Spec. Soc. Japan*, vol. 25, No. 4, pp. 194-200, 1976.

Primary Examiner—William L. Sikes
Assistant Examiner—Matthew W. Koren

[57] ABSTRACT

A light beam having a limited diameter impinges upon and transmits through an object and scattering light carrying information regarding the internal structure or composition of the sample is obtained from the sample. The scattering light is photoelectrically detected by a detecting system through an observation optical system.

11 Claims, 6 Drawing Figures

METHOD OF ANALYZING AN OBJECT BY USE OF SCATTERING LIGHT

This is a continuation of application Ser. No. 009,496, filed Feb. 5, 1979, now abandoned.

BACKGROUND OF THE INVENTION

1. Field of the Invention

This invention relates to a method of analyzing the fine structure or composition of an object by use of scattering of light.

2. Description of the Prior Art

In order to observe the fine structure of an object like a crystal body, it has been known to use various kinds of microscope such as an ordinary optical microscope, polarizing microscope, phase contrast microscope, electron microscope and scanning type electron microscope. In these microscopes, a light beam or an electron beam is caused to impinge upon the surface of an object to be observed and the pattern appearing on the surface in the form of a pattern of different colors or different brightness is observed through the microscope. In other words, in the microscope the structure or composition on the observed surface is represented by a pattern of difference in transmissivity, reflectance or secondary electron emission efficiency. Therefore, the microscope is convenient for generally observing or analyzing a surface of an object.

However, in case of observing arrangements of atoms or lattice defects on a surface of a crystal in the form of a pattern, the conventional microscopes are disadvantageous in that information from different atoms is superposed with the information based on the aimed atoms and further it is not absolutely possible to obtain the same information from the same sample due to influence of the impinging angle of the light beam or electron beam and the anisotropy of the crystal.

In addition, in the transmission type microscope the sample must be made into a thin piece, and in the reflection type microscope the sample must be made to expose a flat surface for observation. These are sometimes inconvenient for some kind of samples.

SUMMARY OF THE INVENTION

It is therefore an object of the present invention to provide a method of accurately analyzing the structure or composition within a body.

More specifically, it is an object of the present invention to provide a method of analyzing the structure or composition on a desired plane within a body without making a sample into a thin piece or without making a sample expose the surface to be analyzed which is capable of classifying the information thus obtained and picking up the necessary kind of information and displaying the picked up information in the form of a pattern representing the observed surface.

The above objects of the present invention are accomplished by causing a light beam transmit through an object to be analyzed and analyzing the scattering light from the object. In this case, in order to prevent the interaction between the scattering light beams, the light impinging upon the object should preferably be stopped down to a predetermined diameter of light flux. Further, the light beam impinging upon the object should preferably be scanned along the predetermined plane within the object to be analyzed in order to obtain information for analysis along the plane. Alternatively, the light may be fixed stationary and the object to be analyzed may be moved in the direction of the plane along which the object is to be analyzed. In the present invention, it is also possible to provide a scanning system in the observing optical system so that the observation may be made scanning along the plane within the object to be analyzed illuminated by light.

The information thus obtained is received by a photosensor and the electric output of the photosensor is computer-processed together with the illuminating light and the scanning signal of the observation system so that the information may be displayed on a CRT or the like. Hence, the microscopic information of the object or sample representing the molecular structure or crystal structure thereof is represented in the form of a pattern and can easily be analyzed.

As the scattering of light utilized by the present invention, an elastic scattering accompanied by no shift of frequency and non-elastic scattering accompanied by a shift of frequency such as Raman scattering, Brillouin scattering and the like are known. The elastic scattering and the non-elastic scattering can be used together for analysis by causing a light beam focused to a predetermined diameter to impinge upon and transmit through a sample crystal and use all the scattering light therefrom as a source of information. In this case, the scattering light includes all the frequency components. This is advantageous in that the existence and distribution of fine particles smaller than the wavelength of the illumination light and the variation in internal refractive index can easily be observed. By scanning the illumination light, the composite information therefore along the scanning plane can be obtained.

Further, in the ordinary optical microscope, it is impossible to discriminate between a near point and a far point within the focal depth of the objective thereof. However, in accordance with the present invention, the discrimination can be made by focusing the illumination light beam to a thin beam having a diameter of $20\mu$ for instance and scanning the light beam to know the position of center of scattering. In the conventional ultramicroscope or dark-field microscope, it is impossible to detect a substance having a small effect of scattering when there is a substance having a very large effect of scattering anywhere in the sample. However, in accordance with the present invention, the detection of a substance of small effect of scattering is always possible as long as there is no substance of large effect of scattering in the optical path of the scanning light beam. Accordingly, it is possible to detect even a small optical abnormal information.

When the non-elastic scattering is used for analysis in the present invention, Raman scattering or laser Raman spectroscopy using a monochromatic light like a laser beam is utilized to obtain molecular structure theoretical information regarding a microscopic part of the sample. The Raman scattering is particularly suitable for living thing samples. In case of the samples containing much water such as the living thing samples, the light in the infrared region is absorbed by the sample and the information based on the molecular vibration is very difficult to detect. In the laser Raman spectroscopy, however, a light beam having a short wave length is used as the carrier wave and the shift of frequency of the scattering light of the short wave length light is detected to obtain information regarding the molecular vibration mode of the sample. Further, this method is advantageous even in case of analyzing crystals as compared with the conventional spectroscopic analyzing method in the sense that the information regarding change in position is easy to obtain. In other words, the information regarding the change in position of the phase transition or local change of the phase transition can be obtained by changing the temperature of the sample, and the analysis of the phase transition can be made based on the change in frequency of the scattering light caused by change in the lattice vibration.

In case of using the Brillouin scattering, the information source is the scattering light accompanied by a frequency shift caused by the interaction between phonons and the illumination light. Therefore, by analyzing the scattering light through spectroscopy or detection, the phase transition of a crystal sample and the glass transition of a high molecular weight substance are effectively analyzed.

The information thus obtained can be displayed in the form of a pattern by use of various kinds of methods such as a simple photographic recording, processing and recording through a polarizer, and a recording of only the scattering light of a predetermined frequency through an interferometer. Further, it is possible to use a photosensor instead of using a photographic camera and display the obtained information through a CRT or an electrophotographic scanning system synchronized with the scanning of the illumination light impinging upon the sample. As for the means for display, a plasma display or liquid crystal can be used.

DESCRIPTION OF THE PREFERRED EMBODIMENTS

Figure 1:
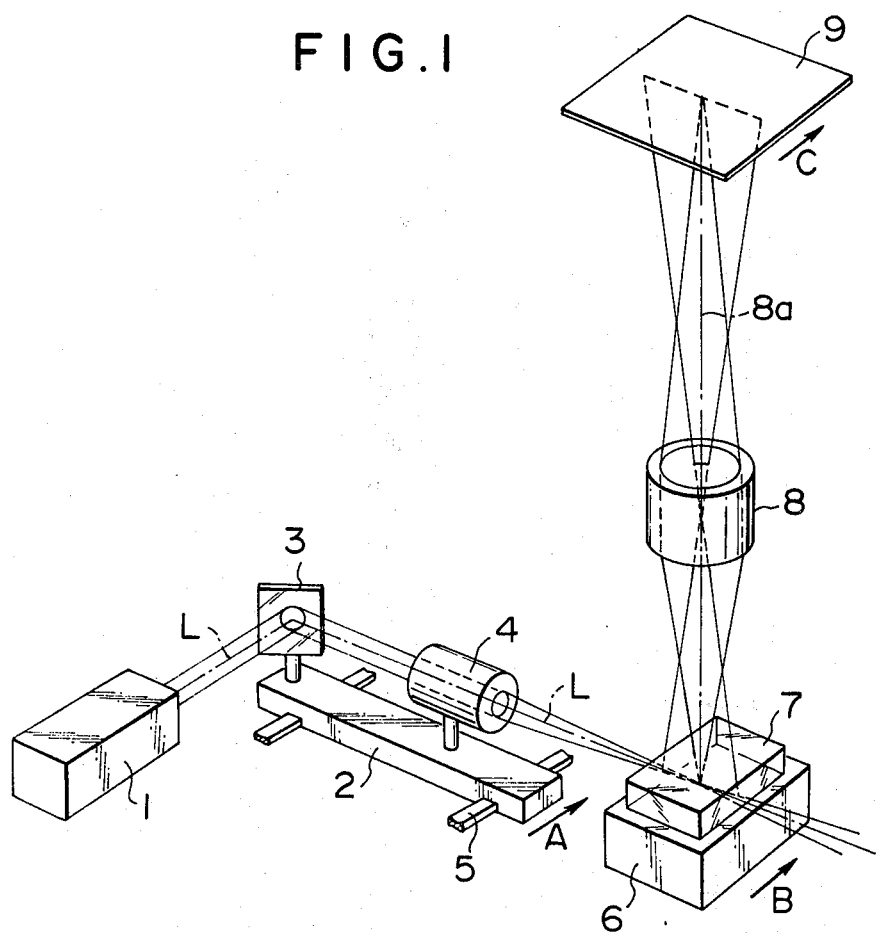
FIG. 1 is a perspective view showing the principle of the present invention embodied in an analyzing device for carrying out the method of this invention.

FIG. 1 shows a basic example of an analyzing system for carrying out the method of the present invention.

In FIG. 1, the analyzing system includes a laser source 1, a carriage 2 carrying a mirror 3 and an optical system 4 fixed thereto, a sample station 6 for supporting thereon a sample 7, a focusing lens system 8, and a photosensitive recording material 9. The carriage 2 is movable in the direction of arrow A being guided by a pair of guide rails 5. The optical axis 8a of the focusing lens system 8 is substantially perpendicular to the axis L of a laser beam emitted by the laser source 1 and reflected by the mirror 3.

The laser beam emitted by the laser source 1 enters the optical system 4 reflected by the mirror 3 and emanates from the optical system 4 as a thin light beam with its cross sectional area limited thereby. The thin laser beam impinges upon the sample 7 mounted on the sample station 6 and transmits therethrough. The laser beam is scattered by the sample 7 when transmitting therethrough, and a part of the scattered laser beam enters the focusing lens system 8 and is focused thereon on a recording material 9. When the sample 7 is a crystal, the scattered laser beam is modified by the structure of the crystal along the path through which it passes. For example, if the refractive index of the sample is changed along the path, colloidal particles exist within the sample along the path, lattice defects exist along the path or the direction of anisotropy is changed along the path, the laser beam passing through the sample would be scattered in the manner which could not be seen in a homogeneous crystal.

The laser beam can be horizontally scanned by moving the carriage 2 carrying the mirror 3 and the optical system 4. Thus, an image which carries the information of the structure of the sample 7 along a sectional plane thereof along which the laser beam is scanned can be recorded on the recording material 9. Preferably, a mask having a slit extending in the direction parallel to the laser beam is positioned immediately in front of the recording material 9 and the recording material 9 is exposed to the scattered laser beam through the slit which is moved in the direction of and in synchronization with the scanning.

Instead of scanning the laser beam, the sample station 6 may be moved in the direction of arrow B. In this case, the recording material 9 is horizontally slid in the direction of arrow C in synchronization with the movement of the sample station 6 taking the magnification of the focusing lens system 8 into account.

When the physical properties of the sample 7 are different depending on the direction, a combination of a polarizing plate positioned between the sample 7 and the optical system 4 and the analyzer positioned between the sample 7 and the focusing lens system 8 are effective to obtain the information of the physical properties.

Figure 2:
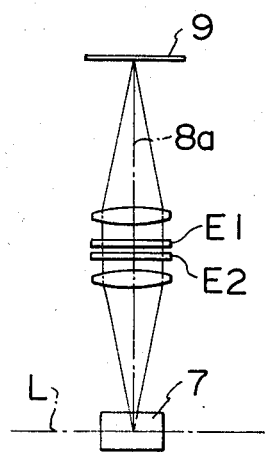
FIG. 2 is a vertical view showing an example of an observation optical system which can be employed in the device as shown in FIG. 1.

FIG. 2 shows an example of the lens system using an etalon plate comprising a pair of plane parallel plates E1 and E2 inserted between focusing lenses. The etalon plate only transmits the light of a selected wave length. Thus, the light of the desired wave length can be picked up of the scattering light, whereby an analysis of Brillouin scattering can also be carried out.

Figure 3:
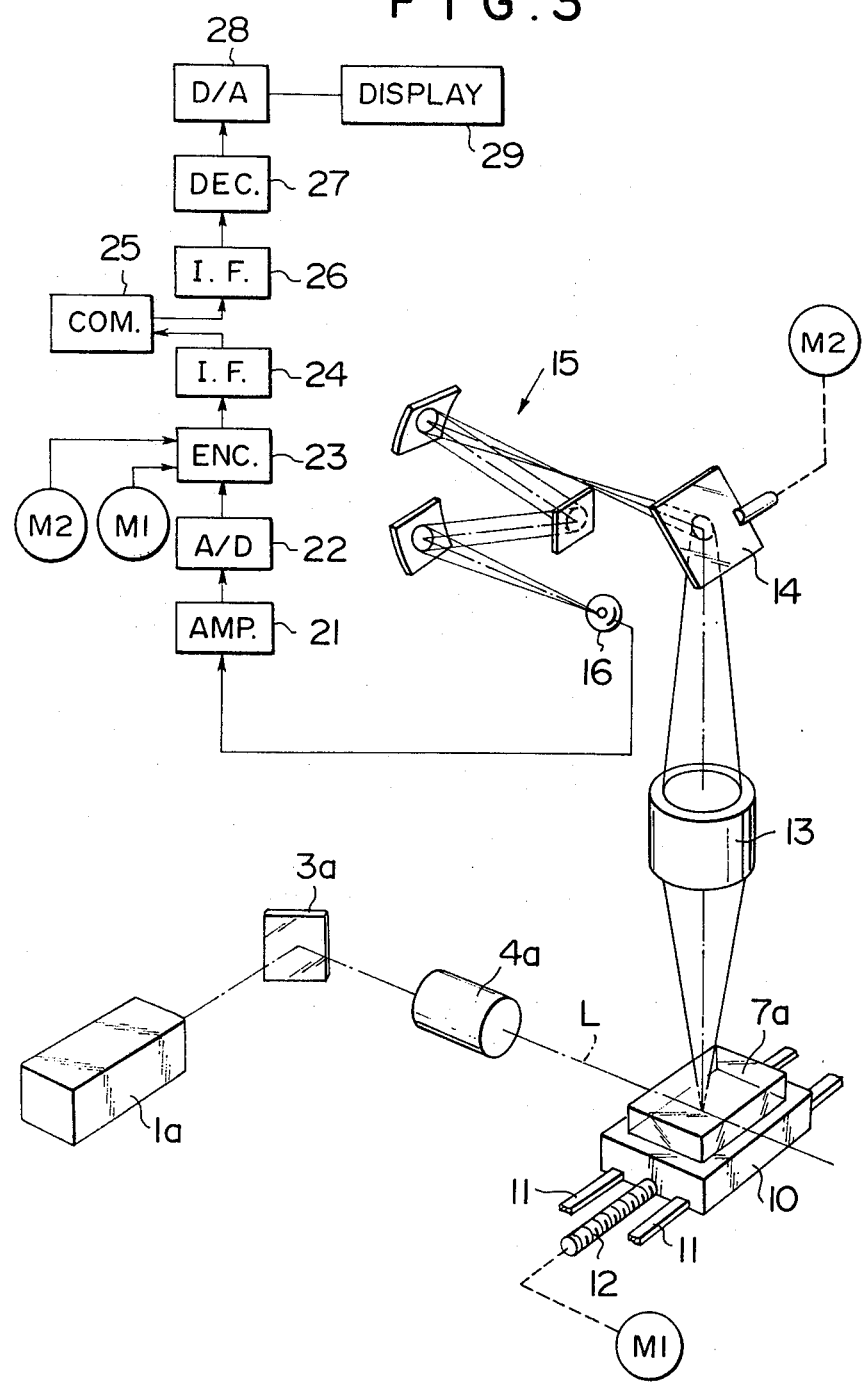
FIG. 3 is a perspective view showing an embodiment of the analyzing device for carrying out the method of the present invention.

FIG. 3 shows an embodiment of the analyzing system for carrying out the present invention suitable for analyzing Raman scattering and Brillouin scattering. Since the analysis of the elastic scattering is normally carried out to analyze a microscopic part of a sample, the focusing lens system should have a magnifying function. In FIG. 3, the laser beam emitted by a laser source 1a passes through a sample 7a positioned on a sample station 10 via a mirror 3a and an optical system 4a. The sample station 10 can be horizontally moved along a pair of guide rails 11 by rotating a screw rod 12. The screw rod 12 is rotated by a motor M1 either continuously or intermittently. The laser beam is scattered by the sample 7a and a part of the scattered laser beam impinges upon a scanning mirror 14 through a magnifying focusing lens 13. The light reflected by the scanning mirror 14 is received by a monochrometer 15, which may be of Czerny-Turner type comprising a pair of pherical concave mirrors and a grating. The monochrometer 15 only transmits the light of a selected wave length. The light of the selected wave length permitted to pass through the monochrometer 15 is received by a photosensor 16. The scanning mirror 14 is periodically swung by a motor M2 to have the light coming from the magnifying focusing lens system 13 scan.

With this arrangement, the information of a microscopic part of the sample 7a carried by the scattering light can be displayed in the form of a pattern by a display device which will be described hereinafter. This can be accomplished by swinging the scanning mirror 14 at a high speed to scan the light from the focusing lens system 13 in the direction of the optical axis L of the laser beam from the optical system 4a or in the direction intersecting with the optical axis L with the sample station 10 being moved at an extremely low speed.

Out of the light received by the monochrometer 15, the light of a specific or selected wave length is picked up and the picked up light impinges upon the photosensor 16. The electric output of the photosensor 16 is amplified by an amplifier 21 and then AD converted through an AD converter 22. The digital information of the scattering light of the specific wave length is inputed into an encoder 23 together with digital drive signals of the motors M1 and M2. The output of the encoder 23 is inputed into an electronic computer 25 through an interface 24. The computer 25 is provided with a memorizing function and provides information of the scattering light with respect to a particular microscopic part of the sample by use of the drive signals of motors M1 and M2 in connection with the existence and intensity of the scattering light of a predetermined frequency or by use of the position signals of the sample station 10 and the scanning mirror 14 in connection with the information from the scattering light. The information thus obtained is displayed through a display device 29 by way of the interface 26, decoder 27 and the DA converter 28.

In accordance with the above described method, it is possible to display different kinds of information simultaneously by displaying the different kinds of information in different colors using a color CRT with the spectral characteristic of the monochrometer 15 changed. In case the sample station 10 is moved in the horizontal direction to get the information of one kind and then the sample 10 is slightly moved in the vertical direction and moved in the horizontal direction to get the information of another kind, two kinds of information can be displayed together.

Figure 4:
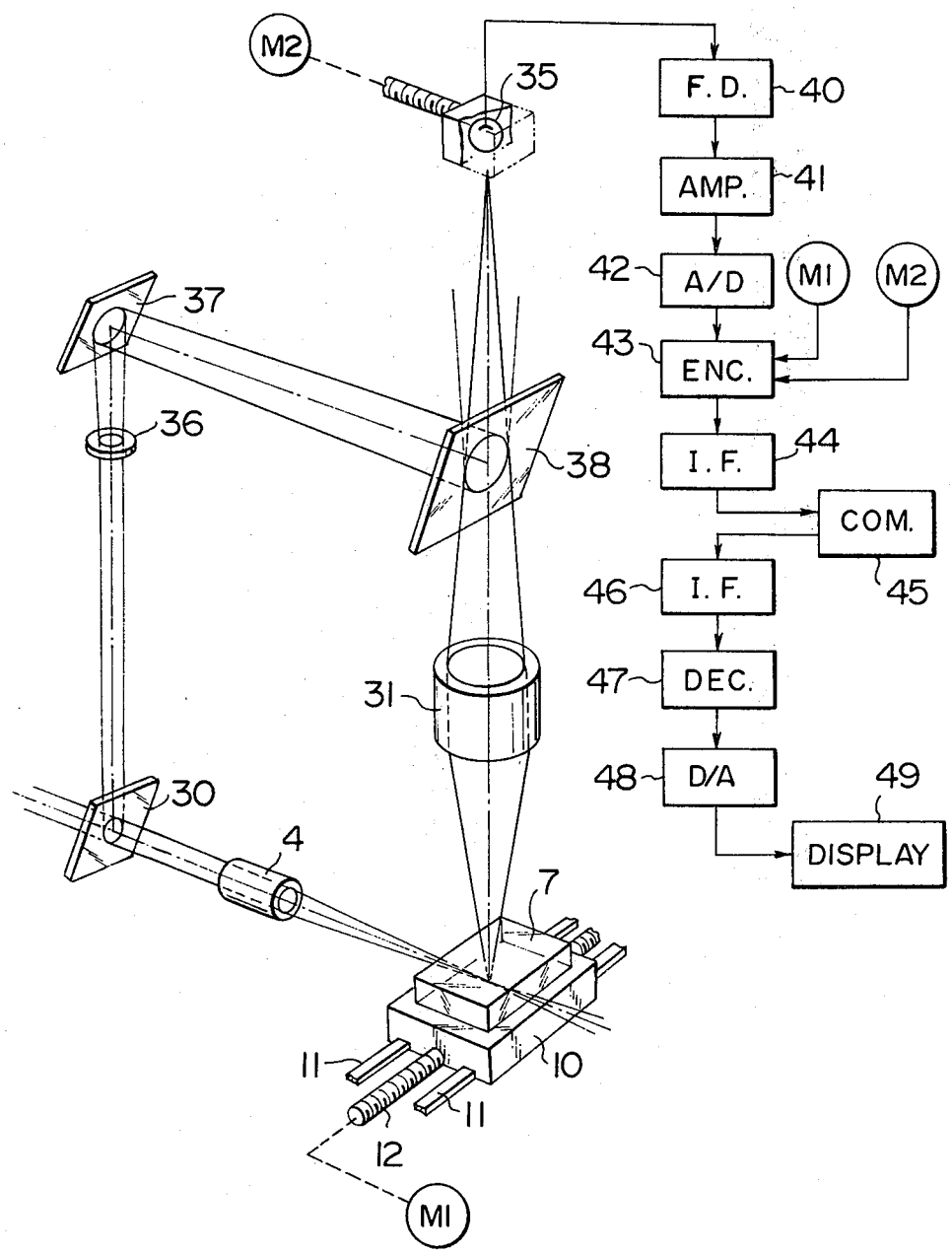
FIG. 4 is a perspective view showing another embodiment of the analyzing device for carrying out the method of the present invention.

FIG. 4 shows another embodiment of the analyzing system for carrying out the present invention provided with a function to pick up light of a predetermined wave length by means of heterodyne detection. Particularly in case of Brillouin scattering or Doppler shifted light, the shift of frequency is extremely small in comparison with the frequency of the illumination light. Therefore, the accuracy in detection must be increased to accurately measure the shift of frequency. In order to conduct the highly accurate detection, in the embodiment shown in FIG. 4 a so-called heterodyne detection is conducted. In FIG. 4, the laser beam guided from the light source is divided by a beam splitter 30 and one of the divided beams impinges upon a sample 7 through an optical system as the embodiment shown in FIG. 3. The sample 7 is held by a sample station 10 movable along rails 11 and moved by means of a feed screw 12 and a motor M. The scattering light from the sample 7 is received by a photosensor 35 through an observation optical system 31 having a magnifying function together with a reference light beam hereinafter described.

The other divided beam divided by the beam splitter 30 is controlled of its diameter through a beam diverging optical system 36 and is guided to the photosensor 35 by way of a mirror 37 and a semitransparent mirror 38 located in the optical path of the observation optical system. Thus, the photosensor 35 receives both the scattering light from the sample 7 and the laser beam impinging upon the sample 7. The output of the photosensor 35 can be accurately detected with reference to the laser beam superposed on the scattering light by way of the mirror 37 and semitransparent mirror 38, whereby only the information of the scattering light can be picked up.

When the shift of frequency of the scattering light is large, the etalon plate is inserted into the observation optical system to select some wave length of light. In this case, the reference light is not necessary. Further, it is possible to pick up only the elastic scattering light and superpose a reference light beam thereon to holographycally record the information and obtain information of the external shape of the sample.

In FIG. 4, a frequency divider 40 is connected with the photosensor 35 and the elements 41 to 49 connected therewith are all equivalent to the elements 21 to 29 as shown in FIG. 3, respectively, and accordingly the detailed description thereof is omitted here.

In the embodiment shown in FIG. 4, the photosensor is directly driven in the observation optical system. This may of course be replaced by the mirror scanning system as shown in FIG. 3. Further, the scanning mirror or the movable photosensor can be replaced by a number of photosensors arranged in an array in the form of a photodiode array as is well known in the art.

In the above embodiments, the direction of the laser beam is horizontal. However, it may be made vertical or oblique. In the observation optical system, an automatic focusing system may be provided to always maintain a good focus.

Figure 5A:
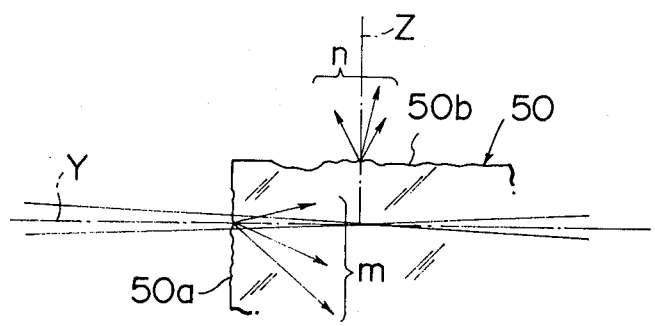
FIG. 5A is an enlarged view showing the surface reflection of light on a sample.
Figure 5B:
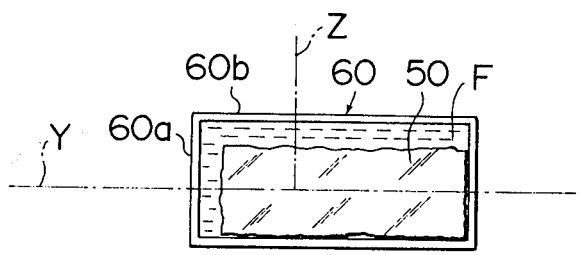
FIG. 5B is an enlarged view for explaining the way of solving the problem as shown in FIG. 5A.

In the sample, the outer surface is often rough as shown in FIG. 5A. In such a case, the incident laser beam Y impinging upon the side surface 50a of a sample 50 is refracted into scattering light m in the sample 50. Further, the light emanating from the sample 50 through the upper surface 50b thereof is also refracted into scattering light n on the sample 50 as shown in FIG. 5A. The scattering light m and n will be a noise or will decrease the amount of light observed, and accordingly lowers the observation efficiency of the analyzing system.

In order to solve the problem, the sample 50 may be put into a container 60 having a flat side and upper surfaces 60a and 60b filled with a liquid F having the same refractive index as that of the sample 50. The upper surface 60b may be omitted when the sample 50 is held still and the face of the liquid F is kept flat. Further, by inclining the container 60 to make the side surface 60a thereof inclined with respect to the incident laser beam Y, multireflection of the incident laser beam at the wall of the container can be prevented.

Further, in order to prevent undesirable reflection of light on the surface of the sample, it is useful to deposit a film of dielectric material on the side surface of the sample 50 for preventing reflection thereon.

We claim:

1. A method of analyzing the internal structure of an object along a desired cross-section comprising steps of causing a light beam transmitting through a desired cross-section of an object to be analyzed, causing the object to move in a direction intersecting with the direction of the light beam so that the plane including said light beam becomes said desired cross-section, creating scattering light which carries information of the internal structure along the path of the light beam transmitting through the object to scan along said cross-section, consecutively observing the scattering light along an optical axis intersecting with said cross-section, and consecutively recording the observed scattering light on a recording medium which is moved in synchronization with the scanning of the light beam, whereby the internal structure of the object is analyzed along said cross-section by summing all the information of the scattering light obtained by the scanning of the light beam.

2. A method of analyzing an object as defined in claim 1 wherein light of a predetermined wave length is picked up from said scattering light as a source of information.

3. A method of analyzing an object as defined in claim 2 wherein said scattering light and a part of said light beam impinging upon the sample are mixed together and the scattering light is picked up from the mixed light by detection.

4. A method of analyzing an object as defined in claim 1 wherein said light beam is scanned along a plane intersecting with said optical axis for observation.

5. A method of analyzing an object as defined in claim 4 wherein said optical axis for observation is scanned along said light beam or in the direction intersecting with the light beam.

6. A method of analyzing an object as defined in claim 4 or 5 wherein light of a predetermined direction of polarization is picked up from said scattering light as a source of information.

7. A method of analyzing an object as defined in claim 4 or 5 wherein said object to be analyzed is put into a container having a flat face at the entrance of light thereof filled with a liquid having the same refractive index as that of the object, whereby the amount of scattering light at the entrance face of the object is reduced.

8. A method of analyzing an object as defined in claim 4 or 5 wherein said object to be analyzed is provided with a film of dielectric material on at least the surfaces intersecting with the incident light beam and with said optical axis of observation, whereby the amount of scattering light at the surfaces of the object is reduced.

9. A method of analyzing an object as defined in claim 4 or 5 wherein said light beam is scanned by moving the object with respect to the light beam the optical path of which is held stationary, the scattering light along said optical axis of observation is focused on a photosensitive material, and the photosensitive material is moved in the direction opposite to the direction of movement of said object in synchronization with the movement of the object, whereby imagewise information along an internal plane of the object is recorded on the photosensitive material.

10. A method of analyzing an object as defined in claim 4 or 5 wherein said scattering light observed is received by a photosensor and the output of the photosensor is displayed in synchronization with the scanning of said light beam.

11. A method of analyzing an object as defined in claim 10 wherein said output of the photosensor is inputed into an electronic computer together with a signal of scanning of said light beam and the output of the computer is displayed.

* * * * *

UNITED STATES PATENT AND TRADEMARK OFFICE
CERTIFICATE OF CORRECTION

PATENT NO. : 4,411,525

DATED : October 25, 1983

INVENTOR(S) : Tomoya Ogawa et al

It is certified that error appears in the above-identified patent and that said Letters Patent are hereby corrected as shown below:

On the title page, Item [75] should read as follows:

-- Inventors: Tomoya Ogawa, Tokyo
Kazuo Moriya, Tokyo
Masane, Suzuki, Saitama-Ken,
Kenji Yasuda, Saitama-Ken,
all of Japan --.

Signed and Sealed this

Seventeenth Day of April 1984

[SEAL]

Attest:

GERALD J. MOSSINGHOFF

Attesting Officer          Commissioner of Patents and Trademarks